United States Patent
Saponas et al.

(10) Patent No.: US 10,076,252 B2
(45) Date of Patent: Sep. 18, 2018

(54) SIZABLE WRIST-WORN PRESSURE SENSING DEVICE

(71) Applicant: Microsoft Technology Licensing, LLC, Redmond, WA (US)

(72) Inventors: T. Scott Saponas, Woodinville, WA (US); Sumit Basu, Seattle, WA (US); Daniel Morris, Bellevue, WA (US); Sidhant Gupta, Seattle, WA (US); Sailaja Malladi, Kirkland, WA (US); Desney S. Tan, Kirkland, WA (US); Nicolas Villar, Cambridge (GB); Shwetak N. Patel, Seattle, WA (US); Gabriel Adam Cohn, Sammamish, WA (US); Jonathan Lester, San Francisco, CA (US); Gregory R. Smith, Bellevue, WA (US); Ronald E. Paulsen, Woodinville, WA (US)

(73) Assignee: MICROSOFT TECHNOLOGY LICENSING, LLC, Redmond, WA (US)

( * ) Notice: Subject to any disclaimer, the term of this patent is extended or adjusted under 35 U.S.C. 154(b) by 381 days.

(21) Appl. No.: 14/750,804

(22) Filed: Jun. 25, 2015

(65) Prior Publication Data
US 2016/0287103 A1    Oct. 6, 2016

Related U.S. Application Data

(60) Provisional application No. 62/142,401, filed on Apr. 2, 2015.

(51) Int. Cl.
A61B 5/02       (2006.01)
A61B 5/022      (2006.01)
(Continued)

(52) U.S. Cl.
CPC ...... *A61B 5/02233* (2013.01); *A61B 5/02108* (2013.01); *A61B 5/02438* (2013.01);
(Continued)

(58) Field of Classification Search
CPC ... A61B 5/02233; A61B 5/6824; A61B 5/681; A61B 5/02438; A61B 5/02108; A61B 5/6831; A61B 5/02444; A61B 2560/0462
See application file for complete search history.

(56) References Cited

U.S. PATENT DOCUMENTS 3,836,759 A * 9/1974 Silverman ................ F21L 2/00
                                                      200/52 R
5,485,848 A    1/1996 Jackson et al.
(Continued)

FOREIGN PATENT DOCUMENTS

CN     104352223 A     2/2015
JP     2002143107 A    5/2002
(Continued)

OTHER PUBLICATIONS

IPEA European Patent Office, Second Written Opinion Issued in PCT Application No. PCT/US2016/025457, dated Feb. 24, 2017, WIPO, 6 Pages.
(Continued)

*Primary Examiner* — Navin Natnithithadha
*Assistant Examiner* — Andrey Shostak
(74) *Attorney, Agent, or Firm* — Alleman Hall Creasman & Tuttle LLP

(57) ABSTRACT

A wrist-worn pressure sensing device includes a pressure sensor. The wrist-worn pressure sensing device also includes a first strap that sets the position of the pressure sensor on a wearer's wrist and a second strap that engages with the first strap to adjust the overall length of the strap without moving the set position of the pressure sensor on the wearer's wrist.

5 Claims, 10 Drawing Sheets

(51) Int. Cl.
  *A61B 5/00* (2006.01)
  *A61B 5/021* (2006.01)
  *A61B 5/024* (2006.01)
  *A44C 5/16* (2006.01)
(52) U.S. Cl.
  CPC .......... *A61B 5/02444* (2013.01); *A61B 5/681* (2013.01); *A61B 5/6824* (2013.01); *A61B 5/6831* (2013.01); *A44C 5/16* (2013.01); *A61B 2560/0462* (2013.01)

(56) References Cited

U.S. PATENT DOCUMENTS

| | | | |
|---|---|---|---|
| 7,341,561 B2 | 3/2008 | Tanaka et al. | |
| 7,674,231 B2 | 3/2010 | McCombie et al. | |
| 2002/0026114 A1* | 2/2002 | Nissila | A61B 5/02438 600/384 |
| 2005/0010119 A1 | 1/2005 | Palti et al. | |
| 2006/0111636 A1 | 5/2006 | Jacober et al. | |
| 2007/0191718 A1* | 8/2007 | Nakamura | A61B 5/0002 600/503 |
| 2008/0021334 A1 | 1/2008 | Finburgh et al. | |
| 2010/0204588 A1 | 8/2010 | Kim et al. | |
| 2010/0286538 A1 | 11/2010 | Kim et al. | |
| 2011/0066049 A1 | 3/2011 | Matsumoto et al. | |
| 2011/0208066 A1 | 8/2011 | Gnadinger | |
| 2012/0179067 A1* | 7/2012 | Wekell | A61B 5/0002 600/587 |
| 2013/0326790 A1 | 12/2013 | Cauwels et al. | |
| 2014/0128753 A1 | 5/2014 | Luna et al. | |
| 2014/0159912 A1 | 6/2014 | Fraden | |
| 2014/0323840 A1* | 10/2014 | Ouwerkerk | A61B 5/0531 600/390 |
| 2014/0364749 A1 | 12/2014 | Varma et al. | |
| 2016/0022210 A1* | 1/2016 | Nuovo | A61B 5/681 600/301 |

FOREIGN PATENT DOCUMENTS

| | | |
|---|---|---|
| KR | 101349767 B1 | 1/2014 |
| KR | 101485700 B1 | 1/2015 |
| KR | 1020150092465 A | 8/2015 |
| KR | 1020160092250 A | 8/2016 |
| KR | 101667412 B1 | 10/2016 |

OTHER PUBLICATIONS

Cossio, Carlos, "A Low-Cost Wristwatch for Non-Invasive Continuous Blood Pressure Monitoring", Published on: Jun. 28, 2013, Available at: http://contest.techbriefs.com/2013/entries/medical/3689-.

"Omron 7 Series Wrist Blood Pressure Monitor", Published on: May 3, 2013, Available at: http://www.amazon.com/Omron-Series-Wrist-Pressure-Monitor/dp/B004D9P1A8.

"BPro®—Radial Pulse Wave Acquisition Device", Retrieved on: Mar. 30, 2015 Available at: http://centerforhearts.com/BPro.html.

ISA European Patent Office, International Search Report and Written Opinion issued in PCT Application No. PCT/US2016/025457, dated Jun. 22, 2016, WIPO, 13 pages.

Morris, Dan et al., "Video-Based Pulse Measurement," U.S. Appl. No. 14/257,671, filed Apr. 21, 2014, 54 pages.

Saponas, T. Scott et al., "Wearable Pulse Pressure Wave Sensing Device," U.S. Appl. No. 14/500,459, filed Sep. 29, 2014, 42 pages.

IPEA European Patent Office, International Preliminary Report on Patentability Issued in PCT Application No. PCT/US2016/025457, dated Jun. 14, 2017, WIPO, 7 Pages.

"H2: The First Wearable Blood Pressure Monitor", Indiegogo Website, Available Online at https://www.indiegogo.com/projects/h2-the-first-wearable-blood-pressure-monitor#/, Available as Early as Oct. 31, 2014, 32 pages.

* cited by examiner

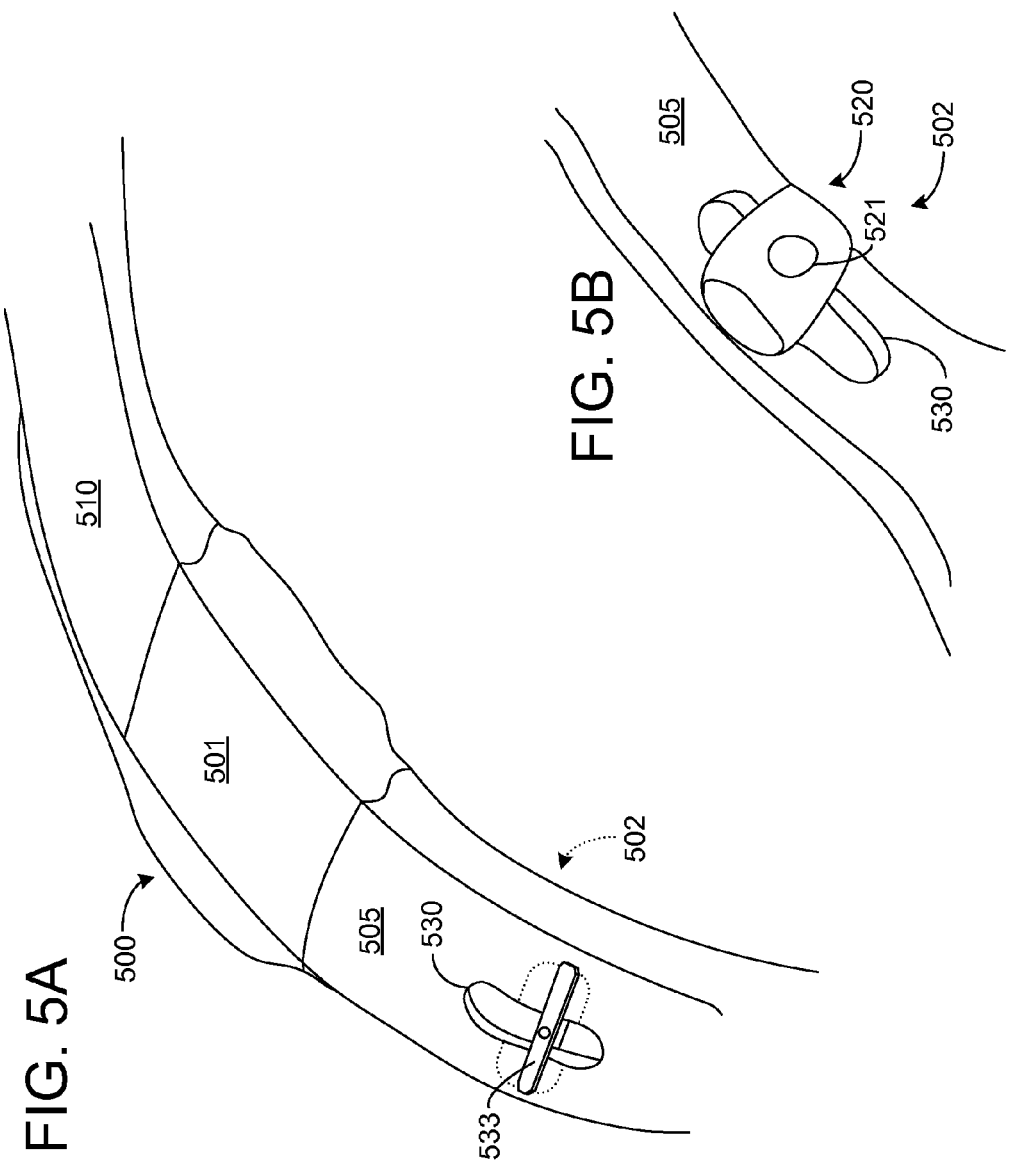

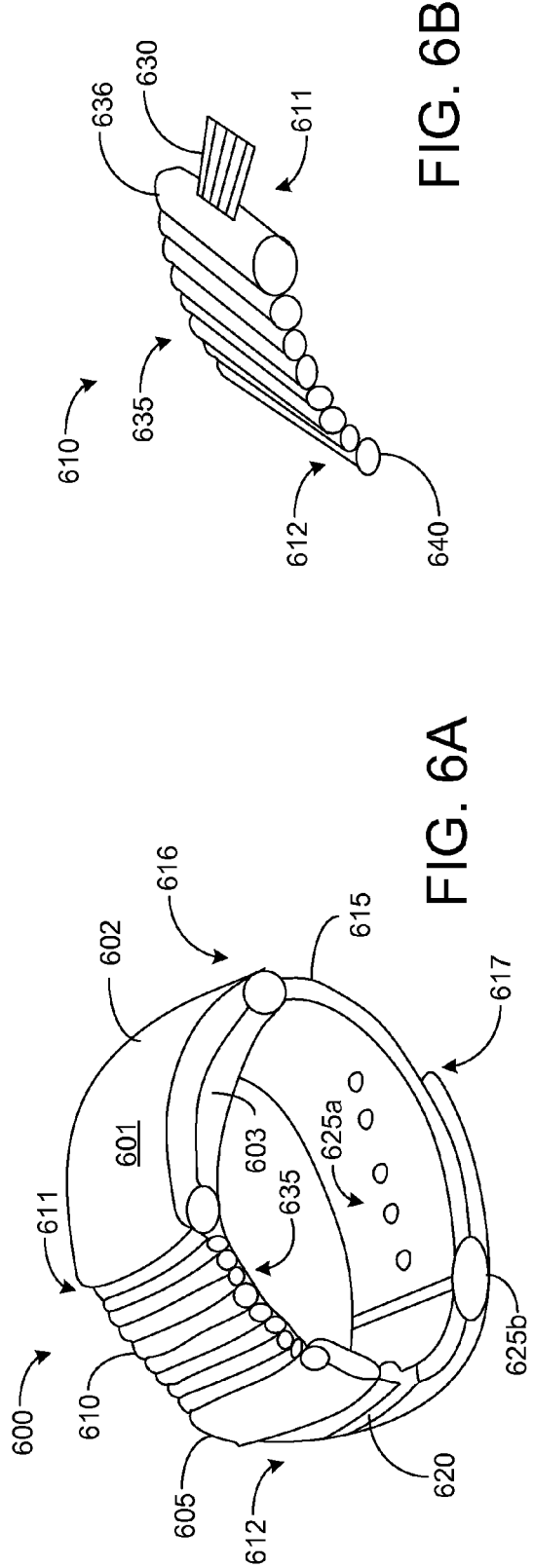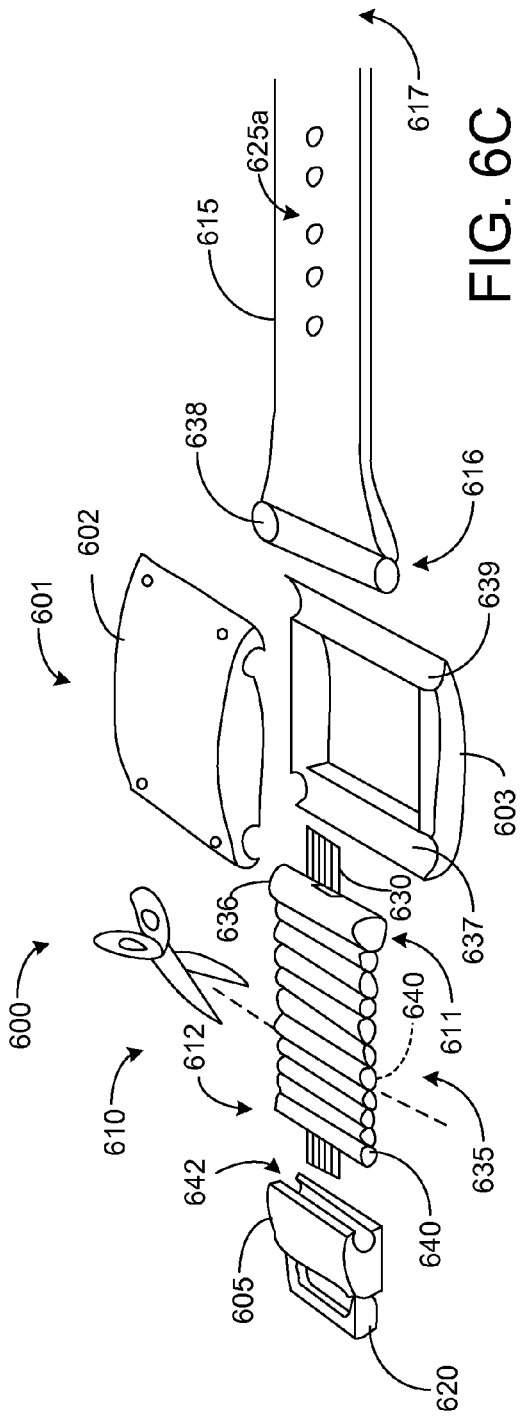

SIZABLE WRIST-WORN PRESSURE SENSING DEVICE

CROSS REFERENCE TO RELATED APPLICATIONS

This application claims priority to U.S. Provisional Patent Application No. 62/142,401, filed Apr. 2, 2015, the entirety of which is hereby incorporated herein by reference.

BACKGROUND

Monitoring heart rate, heart rate variability, arterial blood pressure, pulse-wave velocity, and augmentation index provide useful health information. A pulse pressure wave sensor provides a non-invasive mechanism for capturing the morphology of a pulse pressure wave which can be used in measuring heart rate, heart rate variability, arterial blood pressure, pulse-wave velocity, and augmentation index. A pulse pressure wave sensor may be incorporated into a wearable device.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

A wrist-worn pressure sensing device includes a pressure sensor. The wrist-worn pressure sensing device also includes a first strap that sets the position of the pressure sensor on a wearer's wrist and a second strap that engages with the first strap to adjust the overall length of the strap without moving the set position of the pressure sensor on the wearer's wrist.

BRIEF DESCRIPTION OF THE DRAWINGS

FIGS. 5A-5B show a fourth example of a manually sizable wrist-worn pressure sensing device.

FIGS. 6A-6C show a fifth example of a manually sizable wrist-worn pressure sensing device.

DETAILED DESCRIPTION

Continuous cardiac monitoring of both healthy and unhealthy individuals may increase our understanding of heart disease, atherosclerosis, and other cardiovascular conditions, how these conditions progress, and may thus enable early diagnosis and treatment. Pressure based sensing of the pulse wave offers non-invasive means to extract vital cardiovascular parameters, such as heart rate, heart rate variability, arterial blood pressure, augmentation index, and pulse wave velocity.

However, current non-invasive pulse-pressure sensing techniques rely on trained clinicians employing a handheld instrument on a superficial artery (e.g., radial, carotid, or femoral), and thus do not lend themselves to continuous monitoring. In order to incorporate a pulse-pressure sensor into a wearable device, a sensor must be placed in close contact with an artery. For example, a wrist-wearable device in a watch-like format may place a pressure sensor adjacent to the radial artery. Sizing mechanisms for such a device must accomplish multiple tasks. The device must be sized to properly conform to a wearer's wrist, the pulse-pressure sensing component must be placed directly above the radial artery, and a consistent pressure must be maintained between the pulse-pressure sensing component and the underlying tissue of the wearer without being restrictive or uncomfortable.

This detailed description describes systems and methods for adjusting the size of a wearable pressure sensing device. The wearable pressure sensing device comprises a primary device such as a compute system with a display. The wearable pressure sensing device also includes a pressure sensor located within a satellite device. The wearable pressure sensing device also includes a first strap that can set the position of the pressure sensor on a wearer's wrist at a desired effective length from the primary device. A second strap engages with the first strap in order to adjust the overall length of the strap without moving the set position of the pressure sensor on the wearer's wrist. In some embodiments, powered sizing actuators are included that may be operated to dynamically resize the wrist-worn pressure sensing device responsive to changes in pressure between the pressure sensor and the wrist of a user wearing the device.

Figure 1:
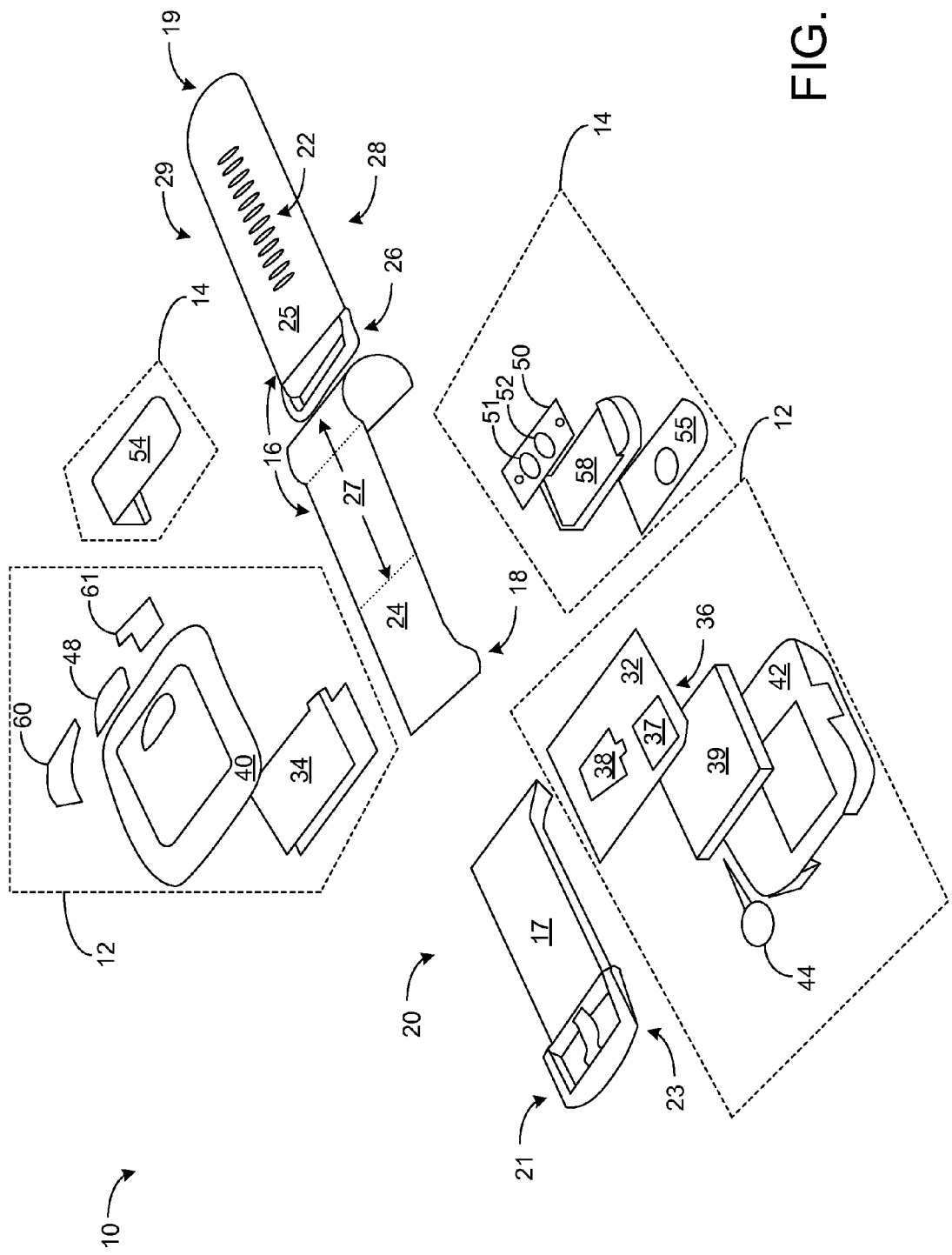
FIG. 1 shows an exploded view of a wearable electronic device.

FIG. 1 shows aspects of an example sensor-and-logic system in the form of a wearable electronic device 10. The wearable electronic device 10 may be configured to measure, analyze, and/or report one or more health/fitness parameters of a wearer of wearable electronic device 10. Wearable electronic device 10 is not limiting. One or more of the features described below with reference to wearable electronic device 10 may be implemented in another sensor-and-logic system, which optionally may have a form factor that differs from wearable electronic device 10.

Wearable electronic device 10 is shown disassembled in order to depict inner componentry. The illustrated device is band-shaped and may be worn around a wrist. Wearable electronic device 10 includes a primary device 12 and a satellite device 14. Components of primary device 12 and satellite device 14 are indicated by dashed outlines. Primary device 12 may have a form function similar to the main body of a watch, and may comprise the primary user interface componentry (e.g., display, inputs, etc.) for wearable electronic device 10. Satellite device 14 may comprise pulse pressure wave transduction componentry that may enable wearable electronic device 10 to function as a wearable cardiovascular monitoring device. The accuracy of pulse pressure wave transduction may be dependent on the placement of the transduction componentry relative to the wearer's skin and underlying tissue and vasculature. For example, including the pulse pressure wave transduction componentry in satellite device 14 may enable pulse pressure wave transduction at the underside of the wearer's wrist while primary device 12 is situated on the back of the wearer's wrist in a position that is familiar to watch-wearers.

Wearable electronic device 10 is shown having a first strap 16 and a second strap 17. However, in some examples a single strap may be included, and in some examples, more than two straps may be included. The straps of wearable electronic device 10 may be elastomeric in some examples, and one or more of the straps optionally may be comprised of a conductive elastomer. First strap 16 may be connected to primary device 12 at first end 18, while second end 19 is located on the opposite, distal end of first strap 16. Similarly, second strap 17 may be connected to primary device 12 at first end 20, while second end 21 is located on the opposite, distal end of second strap 17. First strap 16 comprises primary fastening componentry 22 located towards second end 19, while second strap 17 comprises secondary fastening componentry 23 located towards second end 21. The straps and fastening componentry enable wearable electronic device 10 to be closed into a loop and to be worn on a wearer's wrist.

In this example, first strap 16 comprises a proximal portion 24 which connects to primary device 12 and a distal portion 25 that comprises primary fastening componentry 22. Proximal portion 24 and distal portion 25 may be coupled together via tertiary fastening componentry 26. In this way the distance between primary device 12 and primary fastening componentry 22 may be adjusted. However, in other examples, first strap 16 may be a single continuous strap that both connects to primary device 12 and comprises primary fastening componentry 22.

Satellite device 14 may be attached to first strap 16 at a fixed position within attachment region 27 of first strap 16, thus establishing a fixed distance between primary device 12 and satellite device 14. Primary fastening componentry 22 and secondary fastening componentry 23 are complementary, and thus may be adjustably engaged to adjust the circumference of wearable electronic device 10 without moving the fixed position of satellite device 14 relative to primary device 12. In this example, primary fastening componentry 22 includes discrete locations for engaging with secondary fastening componentry 23. However, in other examples, primary fastening componentry 22 and secondary fastening componentry 23 may be adjustably engaged along a continuous region.

Wearable electronic device 10 comprises a user-adjacent side 28 and an externally facing side 29. As such, primary device 12, satellite device 14, first strap 16, and second strap 17 may each have a user-adjacent side and externally facing side. In the closed conformation, wearable electronic device 10 thus comprises an inner surface (user-adjacent) and an outer surface (externally facing).

Wearable electronic device 10 includes various functional components integrated into primary device 12. In particular, primary device 12 includes a compute system 32, display 34, communication suite 36, and various sensors. These components draw power from one or more energy-storage cells 39. A battery—e.g., a lithium ion battery—is one type of energy-storage cell suitable for this purpose. Examples of alternative energy-storage cells include super- and ultra-capacitors. In wearable electronic devices worn on the wearer's wrist, the energy-storage cells may be curved to fit the wrist.

In general, energy-storage cells 39 may be replaceable and/or rechargeable. In some examples, recharge power may be provided through a universal serial bus (USB) port, which may include a magnetic latch to releasably secure a complementary USB connector. In other examples, the energy-storage cells 39 may be recharged by wireless inductive or ambient-light charging. In still other examples, the wearable electronic device 10 may include electro-mechanical componentry to recharge the energy-storage cells 39 from the wearer's adventitious or purposeful body motion. For example, batteries or capacitors may be charged via an electromechanical generator integrated into wearable electronic device 10. The generator may be turned by a mechanical armature that turns while the wearer is moving and wearing wearable electronic device 10.

Within primary device 12, compute system 32 is situated below display 34 and operatively coupled to display 34, along with communication suite 36, and various sensors. The compute system 32 includes a data-storage machine 37 to hold data and instructions, and a logic machine 38 to execute the instructions. Aspects of compute system 32 are described in further detail with reference to FIG. 9. These components may be situated within primary device 12 between top device housing frame 40 and bottom device housing frame 42. Primary device 12 may further comprise other actuators that may be utilized to communicate with the wearer, such as haptic motor 44, and/or a loudspeaker (not shown).

Display 34 may be any suitable type of display. In some configurations, a thin, low-power light emitting diode (LED) array or a liquid-crystal display (LCD) array may be used. An LCD array may be backlit in some implementations. In other implementations, a reflective LCD array (e.g., a liquid crystal on silicon, (LCOS) array) may be frontlit via ambient light. A curved display may also be used. Further, active-matrix organic light-emitting diode (AMOLED) displays or quantum dot displays may be used.

Communication suite 36 may include any appropriate wired or wireless communication componentry. In some examples, the communication suite 36 may include a USB port, which may be used for exchanging data between wearable electronic device 10 and other computer systems, as well as providing recharge power. The communication suite 36 may further include two-way short-range radio transmission (e.g., BLUETOOTH), local area networking (e.g., WI-FI), cellular, near-field communication and/or other radios. In some implementations, communication suite 36 may include an additional transceiver for optical (e.g., infrared) communication.

In wearable electronic device 10, a touch-screen sensor may be coupled to display 34 and configured to receive touch input from the wearer. The touch-screen sensor may be resistive, capacitive, or optically based. Pushbutton sensors may be used to detect the state of push button 48, which may include rockers. Input from the pushbutton sensor may be used to enact a home-key or on-off feature, control audio volume, turn a microphone on or off, etc.

Wearable electronic device 10 may include a plurality of additional sensors. Such sensors may include one or more microphones, visible-light sensors, ultraviolet sensors, and/or ambient temperature sensors. A microphone may provide input to compute system 32 that may be used to measure the ambient sound level or receive voice commands from the wearer. Input from the visible-light sensor, ultraviolet sensor, and ambient temperature sensor may be used to assess aspects of the wearer's environment—i.e., the temperature, overall lighting level, and whether the wearer is indoors or outdoors.

A secondary compute system 50 is located within satellite device 14. Secondary compute system 50 may include a data-storage machine 51 to hold data and instructions, and a logic machine 52 to execute the instructions. Secondary compute system 50 may be situated between top satellite housing frame 54 and bottom satellite housing frame 55. Top satellite housing frame 54 and bottom satellite housing frame 55 may be configured to couple satellite device 14 to a fixed position within attachment region 27 on first strap 16 through the use of screws, bolts, clamps, etc. Top satellite housing frame 54 and bottom satellite housing frame 55 are shown as separate components, but in some examples, they may be coupled together by a hinge on one end, allowing satellite device 14 to be latched together around first strap 16 at the other end.

Secondary compute system 50 may be communicatively coupled to compute system 32. Satellite device 14 may mediate communication between secondary compute system 50 and compute system 32. For example, satellite device 14 may include one or more conductive contacts configured to physically intersect with one or more conductive wires extending from primary device 12 through attachment region 27 within first strap 16. In other examples, secondary compute system 50 may be coupled to compute system 32 via capacitive contact between one or more conductive contacts on satellite device 14 and one or more conductive wires within first strap 16. In other examples, a ribbon cable may extend from primary device 12 through first strap 16 such that one or more contacts on satellite device 14 can intersect with the ribbon cable when the satellite device 14 is affixed to first strap 16. In some examples, secondary compute system 50 may communicate with compute system 32 via wireless communication. In some examples, satellite device 14 may include one or more energy-storage cells. In other examples, satellite device 14 and components housed therein may draw power from energy-storage cells 39.

A pressure transducing device 58 is located within satellite device 14. When placed above the wearer's radial artery, the pressure transducing device 58 may transduce a pulse pressure wave present in the radial artery, thus functioning as a radial tonometer. The transduced pulse pressure waves may then be converted into pulse waveform signals and utilized to determine the wearer's heart rate, blood pressure, and other cardiovascular properties. Attachment region 27 may comprise a plurality of possible sensing locations, each possible sensing location having a different effective distance from primary device 12 along the first strap 16. In some examples, attachment region 27 may comprise a plurality of continuous possible sensing locations, while in other examples attachment region 27 may comprise a plurality of discrete possible sensing locations. By adjusting the distance between primary device 12 and satellite device 14, satellite device 14 and pressure transducing device 58 may be placed directly over the wearer's radial artery while primary device 12 is positioned on the back of the wearer's wrist. In some examples, satellite device 14 may be coupled to first strap 16 at a fixed position (e.g., at second end 19). In such examples, the distance between satellite device 14 and primary device 12 may be adjusted via interactions between satellite device 14 and first strap 16, via interactions between first strap 16 and primary device 12, and/or between regions of first strap 16.

Bottom satellite housing frame 55 is shown with an opening through which pressure transducing device 58 can establish contact with the wearer's wrist at the radial artery. Wearable electronic device 10 may be configured to instruct the wearer to adjust the position of satellite device 14 relative to the radial artery if a pressure detected by the pressure transducing device 58 is below a threshold, and/or if a signal quality of the transduced pressure is below a threshold. In some examples, wearable electronic device 10 may be configured to self-adjust the position of satellite device 14 and/or the overall circumference of wearable electronic device 10.

In some examples, pressure transducing device 58 may be housed and configured to interface with a wearer's wrist independently from primary device 12. For example, pressure transducing device 58 may be worn on one wrist, while primary device 12 may be worn on the other wrist. In other examples, pressure transducing device 58 may be configured to be worn while primary device 12 is not worn. Pressure transducing device 58 may thus be configured to communicate with one or more additional computing devices, (e.g., via secondary compute system 50) such as a personal computer, tablet computer, smart phone, smart watch, gaming device, etc.

FIG. 1 shows a pair of contact sensor modules 60 and 61 situated on top device housing frame 40, which may be touchable by a wearer using fingers on the hand opposite the wrist where wearable electronic device 10 is worn. In some examples, other contact sensor modules may be included in addition to or as an alternative to contact sensor modules 60 and 61. As one example, other contact modules may be attached to user-adjacent side 28 of primary device 12, first strap 16 and/or second strap 17, and thus be held in contact with points on the wearer's wrist when wearable electronic device 10 is worn. As another example, one or more contact modules may be situated at or near secondary fastening componentry 23 on the externally-facing side 29 of wearable electronic device 10 when wearable electronic device 10 is closed into a loop, thus allowing the wearer to contact a point on their body reachable with the underside of the wearer's wrist. Additionally or alternatively, one or more contact modules may be situated on the externally-facing side 29 of the loop at first strap 16 and/or second strap 17.

Contact sensor modules 60 and 61 may include independent or cooperating sensor elements, to provide a plurality of sensory functions. For example, contact sensor modules 60 and 61 may provide an electrical resistance and/or capacitance sensory function, which measures the electrical resistance and/or capacitance of the wearer's skin. Compute system 32 may use such input to assess whether or not the device is being worn, for instance. In some implementations, the sensory function may be used to determine how tightly wearable electronic device 10 is being worn. In some examples, a contact sensor module may also provide measurement of the wearer's skin temperature. In some examples, contacting multiple contact sensor modules may allow compute system 32 to determine an electrocardiogram (EKG) of the wearer.

Wearable electronic device 10 may also include motion sensing componentry, such as an accelerometer, gyroscope, and magnetometer. The accelerometer and gyroscope may furnish acceleration data along three orthogonal axes as well as rotational data about the three axes, for a combined six degrees of freedom. This sensory data can be used to provide a pedometer/calorie-counting function, for example. Data from the accelerometer and gyroscope may be combined with geomagnetic data from the magnetometer to further define the inertial and rotational data in terms of geographic orientation. The wearable electronic device 10 may also include a global positioning system (GPS) receiver for determining the wearer's geographic location and/or velocity. In some configurations, the antenna of the GPS receiver may be relatively flexible and extend into straps 16 and/or 17. In some examples, data from the motion sensing componentry may be utilized to determine a position of the wearable electronic device 10, contact modules 60 and or 61, and/or pressure transducing device 58 relative to predetermined sensing locations on the body of the device wearer.

In some examples, wearable electronic device 10 may also include one or more optical sensors paired with one or more optical sources. The optical sources may be configured to illuminate the skin and/or the underlying tissue and blood vessels of the wearer, while the optical sensors may be configured to detect illumination reflected off of the skin and/or the underlying tissue and blood vessels of the wearer. This optical data may be communicated to compute system 32, where the data may be used to determine the wearer's blood-oxygen level, pulse, blood glucose levels, or other biometric markers with optical signatures.

Compute system 32, via the sensory functions described herein, is configured to acquire various forms of information about the wearer of wearable electronic device 10. Such information must be acquired and used with utmost respect for the wearer's privacy. Accordingly, the sensory functions may be enacted subject to opt-in participation of the wearer. In implementations where personal data is collected on the device and transmitted to a remote system for processing, that data may be anonymized. In other examples, personal data may be confined to the wearable electronic device, and only non-personal, summary data transmitted to the remote system.

Figure 2A:
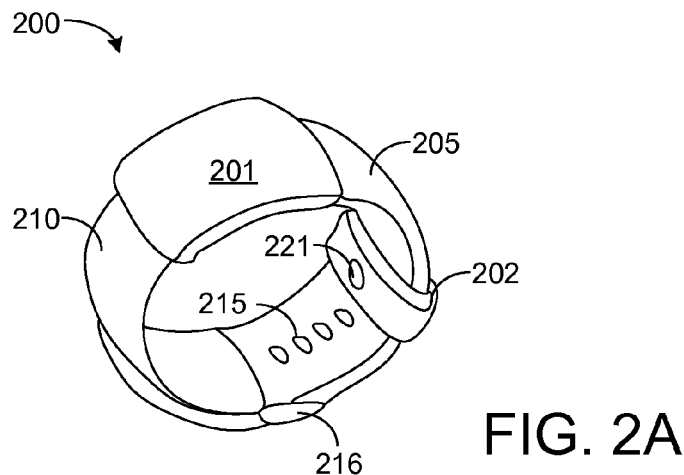
FIGS. 2A-2D show a first example of a manually sizable wrist-worn pressure sensing device.
Figure 2B:
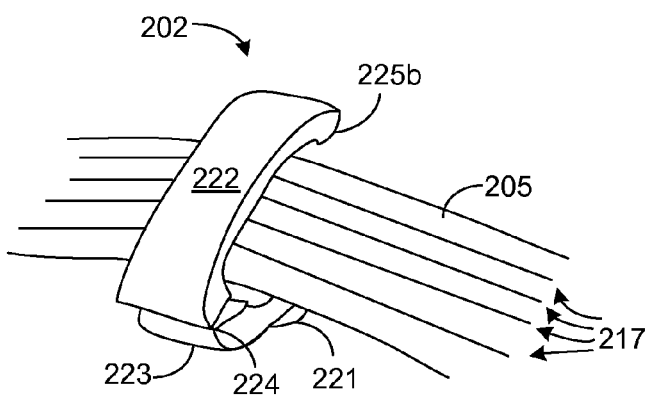
Figure 2C:
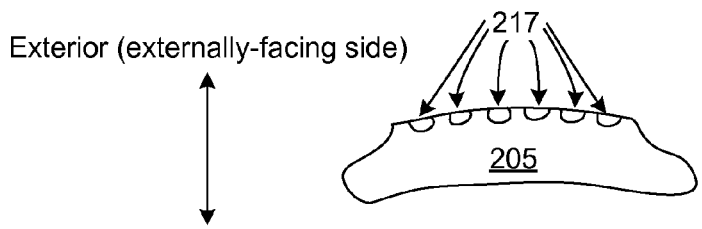
Figure 2D:
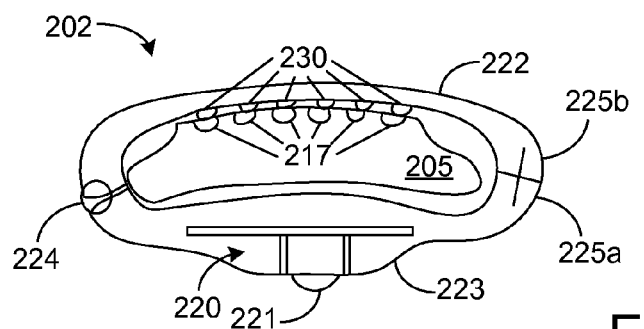

FIGS. 2A-2D show an example wearable pressure sensing device 200. Wearable pressure sensing device 200 includes a primary device 201, a satellite device 202, a first strap 205 and a second strap 210. Straps 205 and 210 each have a first end connected to primary device 201. Primary fastening componentry 215 is located at a second end of first strap 205, while secondary fastening componentry 216 is located at a second end of second strap 210. The straps and fastening componentry enable the wearable pressure sensing device to be closed into a loop and to be worn on a wearer's wrist. First strap 205 includes conductive wires 217. As shown in FIG. 2C, conductive wires 217 are located at the externally facing side (outer surface) of first strap 205 (e.g., away from the wrist of the wearer), but in other configurations, conductive wires 217 may be located at the user-adjacent surface (inner surface) of first strap 205. In some examples, the conductive wires may be located slightly below the surface of first strap 205. Each conductive wire may be located at the base of a slit or groove in the strap, allowing for the conductive wires to be exposed responsive to applied pressure. In this way, the exposure of the conductive wires to sweat, dirt, etc. is reduced. In other examples, first strap 205 may be a conductive elastomer with one or more discrete traces, and individual wires may be omitted.

Satellite device 202 includes pressure transducer assembly 220. A flexible cap 221 protrudes from the body of satellite device 202 such that it may be in contact with the skin of a wearer when wearable pressure sensing device 200 is worn. Pressure applied to the flexible cap may then be conducted to a pressure transducer within pressure transducer assembly 220. In particular, when the flexible cap is positioned over the radial artery of a wearer, pulse-pressure waves may be conducted to the pressure transducer.

Satellite device 202 includes an upper portion 222 and a lower portion 223. Pressure transducer assembly 220 is included in lower portion 223. Upper portion 222 and lower portion 223 are connected at one end by hinge 224. The opposite ends include fastening members 225a and 225b, which allow for upper portion 222 and lower portion 223 to couple together around first strap 205. Satellite device 202 may thus be clamped onto first strap 205 at a fixed distance from primary device 201. This may allow flexible cap 221 to be positioned above the radial artery while primary device 201 is located at the back of the wearer's wrist.

Upper portion 222 includes conductive contacts 230. When satellite device 202 is clamped around first strap 205, conductive contacts 230 engage with conductive wires 217. In configurations where conductive wires 217 are located below the surface of first strap 205, clamping satellite device 202 to first strap 205 may apply pressure to the strap, thus exposing the conductive wires, and allowing contact between conductive wires 217 and conductive contacts 230. In this way, satellite device 202 may be conductively coupled to primary device 201, enabling communication between the primary device and the satellite device, and allowing satellite device 202 to be powered by an energy storage device located within primary device 201. First strap 205 may be of sufficient length to allow satellite device 202 to be placed at a distance from primary device 201 so as to accommodate positioning of flexible cap 221 above the wearer's radial artery without interference from primary fastening componentry 215 or secondary fastening componentry 216. A plurality of possible sensing locations may thus be defined by regions of first strap 205 wherein conductive contacts 230 may engage with conductive wires 217. When satellite device 202 has been securely attached to first strap 205 at a selected sensing location, primary fastening componentry 215 and secondary fastening componentry 216 may be adjustably engaged to adjust the circumference of wrist-worn pressure sensing device 200 without moving satellite device 202 from the selected sensing location.

In some examples, second strap 210 may include conductive wires in addition to first strap 205. In such a configuration, satellite device 202 may be clamped to either first strap 205 or second strap 210, allowing the positioning of flexible cap 221 over the wearer's radial artery when wearable pressure sensing device 200 is worn on either arm. In some examples, satellite device 202 may only be clamped to either first strap 205 or second strap 210, but the orientation of primary device 201 and/or a display device included in primary device 201 may be reversible in orientation, and may be adjusted based on the wearing arm and preferences of the wearer.

FIGS. 3A-3D show another example wearable pressure sensing device 300. Similarly to wearable pressure sensing device 200, wearable pressure sensing device 300 includes a primary device 301, a satellite device 302, a first strap 305 and a second strap 310. Straps 305 and 310 each have a first end connected to primary device 301. Primary fastening componentry 315 is located at a second end of first strap 305 while secondary fastening componentry 316 is located at a second end of second strap 310. The straps and fastening componentry enable the wearable pressure sensing device to be closed into a loop and to be worn on a wearer's wrist. Satellite device 302 comprises pressure transducer assembly 320, which includes flexible cap 321 conductively coupled to a pressure transducer within pressure transducer assembly 320. Satellite device 302 includes an upper portion 322 and a lower portion 323 which are connected at one end by hinge 324, and may be coupled together at the other, opposite end by fastening members 325a and 325b. Satellite device 302 may thus be clamped onto first strap 305 at a fixed distance from primary device 301.

Figure 3A:
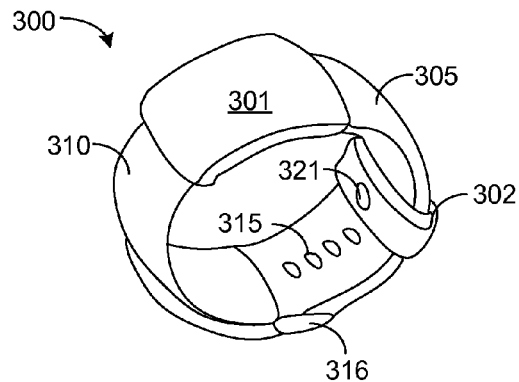
FIGS. 3A-3D show a second example of a manually sizable wrist-worn pressure sensing device.
Figure 3B:
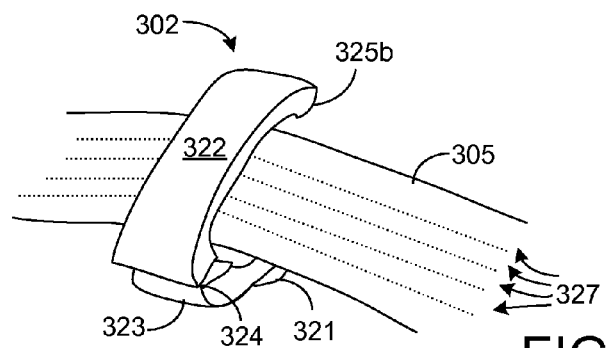
Figure 3C:
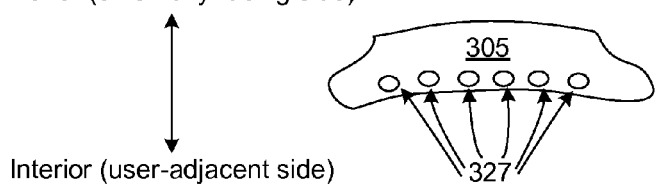
Figure 3D:
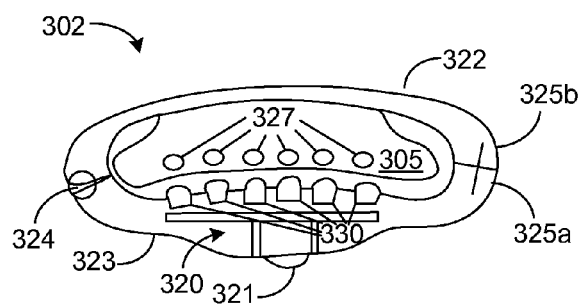

In this example, first strap 305 includes conductive wires 327 embedded within the strap. As shown in FIG. 3C, the conductive wires may be located near the inner (user-adjacent side) surface of first strap 305, and may be covered by a thin elastomeric skin. Satellite device 302 includes conductive contacts 330 protruding from lower portion 323. When satellite device 302 is clamped around first strap 305, conductive contacts 330 capacitively engage with conductive wires 327. Satellite device 302 may be configured to decode signals driven through conductive wires 327 to enable capacitive engagement between conductive wires 327 and conductive contacts 330. Clamping satellite device 302 to first strap 305 may compress first strap 305, thus reducing the distance between conductive contacts 330 and conductive wires 327. Accordingly, satellite device 302 may be capacitively coupled to primary device 301, enabling communication and/or power transfer between the two devices via first strap 305. A plurality of possible sensing locations may thus be defined by regions of first strap 305 where conductive contacts 330 may engage with conductive wires 317. Satellite device 302 may be securely attached to first strap 305 at a selected sensing location of the plurality of possible sensing locations.

FIGS. 4A-4D show another example wearable pressure sensing device 400. Similar to wearable pressure sensing devices 200 and 300, wearable pressure sensing device 400 includes a primary device 401, a satellite device 402, a first strap 405 and a second strap 410. Straps 405 and 410 each have a first end connected to primary device 401. Primary fastening componentry 415 is located at a second end of first strap 405 while secondary fastening componentry 416 is located at a second end of second strap 410. The straps and fastening componentry enable the wearable pressure sensing device to be closed into a loop and to be worn on a wearer's wrist. Satellite device 402 comprises pressure transducer assembly 420, which includes flexible cap 421 conductively coupled to a pressure transducer within pressure transducer assembly 420. Satellite device 402 includes an upper portion 422 and a lower portion 423 which are connected at one end by hinge 424, and may be coupled together at the other opposite end by fastening members 425a and 425b. Satellite device 402 may thus be clamped onto first strap 405 at a fixed distance from primary device 401.

Figure 4A:
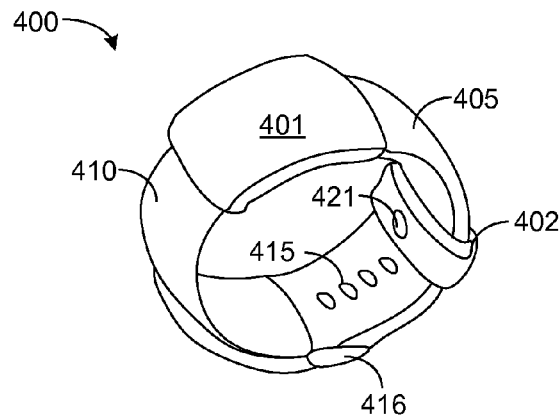
FIGS. 4A-4D show a third example of a manually sizable wrist-worn pressure sensing device.
Figure 4B:
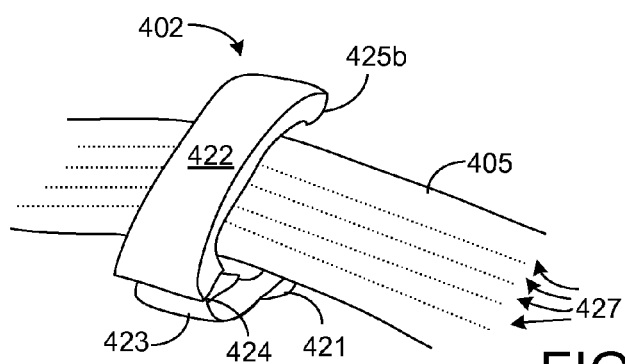
Figure 4C:
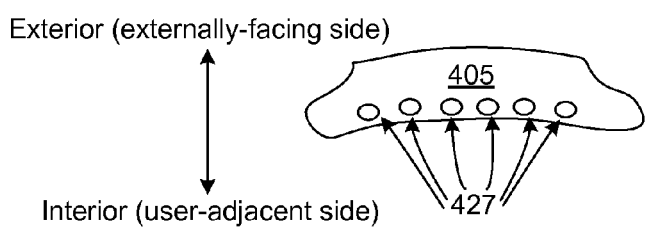
Figure 4D:
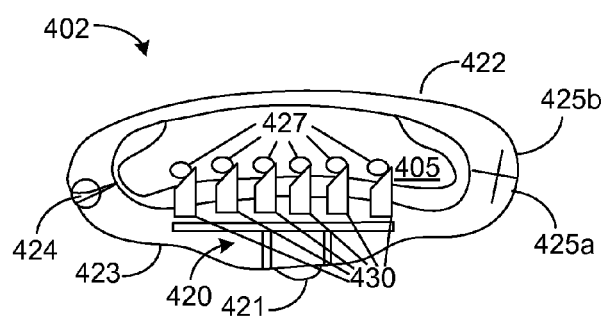

In this example, first strap 405 includes conductive wires 427 located within the strap. As shown in FIG. 4C, the conductive wires may be located near the inner (user-adjacent side) surface of first strap 405, and may be covered by a thin elastomeric skin. Satellite device 402 includes piercing conductive contacts 430 protruding from lower portion 423. When satellite device 402 is clamped around first strap 405, piercing conductive contacts 430 penetrate first strap 405, inducing physical contact with conductive wires 427. First strap 405 may be composed of a self-sealing elastomer, allowing for punctures in the strap to close around piercing conductive contacts 430, thus reducing the exposure of conductive wires 427. First strap 405 optionally may be replaced if the distance between satellite device 402 and primary device 401 is to be subsequently adjusted (e.g., elastomeric straps stretch, wearer gains or loses weight, etc.).

FIGS. 5A-5B show another example wearable pressure sensing device 500. Wearable pressure sensing device 500 includes primary device 501, satellite device 502, first strap 505, and second strap 510. First strap 505 and second strap 510 may be joinable at their respective ends distal from primary device 501 via fastening componentry (not shown). Satellite device 502 includes pressure transducer 520 and flexible cap 521.

As shown in FIG. 5B, satellite device 502 may be coupled to first strap 505 by insertion through groove 530. Groove 530 also allows satellite device 502 to be moved closer to or farther away from primary device 501 in order to allow placement of flexible cap 521 above the radial artery of a user wearing sensing device 500. In the illustrated example, placement of satellite device 502 relative to first strap 505 may be secured by back clamp 533. Back clamp 533 and satellite device 502 are cooperatively configured to clasp first strap 505 and thereby fix the distance between the satellite device and the primary device 501. In other implementations, other fixing mechanisms may be used. The satellite device may be communicatively coupled to the primary device in any suitable manner, including those described above.

While the examples described with reference to FIGS. 1, 2A-2D, 3A-3D, 4A-4D, and 5A-5C describe various mechanisms for transferring power and/or data between a primary device and a satellite device, they are by no means limiting. One or both of power and data may be transferred via wires and/or wirelessly. Wireless communication may be used to communicatively couple a primary device and a satellite device using capacitive data transfer, as described with reference to FIGS. 4A-4D, ultrasonic data transfer, inductive data transfer, whereby inductive coils are deposed within both the primary device and satellite device, RF, and/or other wireless communication methods. Power may be wirelessly transferred using inductive coils deposed within both the primary device and satellite device. In some examples where inductive power transfer is utilized, the power transfer signal may be modulated to further enable wireless communications.

FIGS. 6A-6C show another example wearable pressure sensing device 600. Wearable pressure sensing device 600 includes primary device 601, which comprises top device housing 602 and bottom device housing 603. Wearable pressure sensing device 600 further includes satellite device 605, which comprises a pressure transducer assembly.

First strap 610 comprises a first end 611 that may be connected to primary device 601, and a second end 612 that may be coupled to satellite device 605. Second strap 615 comprises a first end 616 that may be connected to primary device 601, and a second end 617. In this example, primary fastening componentry 620 is connected to second end 612 of first strap 610 via satellite device 605, while second strap 615 comprises secondary fastening componentry 625a and 625b.

Second strap 615 may adjustably engage primary fastening componentry 620. In this example, primary fastening componentry 620 is shown as a buckle through which second strap 615 may be passed through, thus allowing secondary fastening componentry 625a and 625b to adjustably engage, forming wearable pressure sensing device 600 into a loop.

As shown in FIGS. 6B and 6C, first strap 610 may include a central ribbon cable 630, which may connect to primary device 601 at first end 611 and to satellite device 605 at second end 612. Central ribbon cable 630, or another suitable conductor, may be configured to form an inductive or conductive electrical connection between primary device 601 and satellite device 605. In some implementations, the central ribbon cable 630 may be pierced and/or sandwiched by complementarily configured contacts and/or inductive clamps.

First strap 610 may include a series of links 635. One or more of links 635 may be removed from first strap 610, thus physically shortening the length of first strap 610, and adjusting the effective distance between satellite device 605 and primary device 601. Central ribbon cable 630 may be configured to be trimmed independently from or at different lengths than links 635 so that an end of the central ribbon cable remains exposed for electrical connection to the satellite device 605. For example, one or more links 635 may be removed before the central ribbon cable is trimmed, so that the user can test the sizing/positioning of the adjusted strap. In some examples, additional links may be added to first strap 610, provided that an end of central ribbon cable 630 remains exposed, or is otherwise extended through the additional links. Alternatively, a shorter ribbon cable may be replaced with a longer ribbon cable. Once satisfied with the sizing/positioning, the central ribbon cable 630 may be trimmed and/or otherwise prepared for electrical attachment to the satellite device 605.

First strap 610 and second strap 615 may include connective componentry that mediate connection to the primary device. For example, first strap 610 may couple to primary device 601 at first end 611 via primary end link 636 by placing primary end link 636 in a groove 637 created by top device housing 602 and bottom device housing 603. Similarly, second strap 615 may couple to primary device 601 at first end 616 by placing coupling link 638 in groove 639. At the second end 612 of first strap 610, the terminal link 640 that results following any link removal may be coupled to satellite device 605 via groove 642.

Each link 635 may be configured to engage with groove 642 when occupying the position of terminal link 640. In this way, the position of satellite device 605 relative to primary device 601 may be adjusted by physically altering the length of first strap 610, while maintaining the connective componentry of first strap 610 that mediates connecting first end 611 of first strap 610 to primary device 601, as well as the connective componentry that mediates connecting second end 612 of first strap 610 to satellite device 605. Secondary fastening componentry 625 may be used to adjust the circumference of wearable pressure sensing device 600 without moving the fixed position of satellite device 605 relative to primary device 601 by adjustably engaging secondary fastening componentry 625 with primary fastening componentry 620.

Figure 7A:
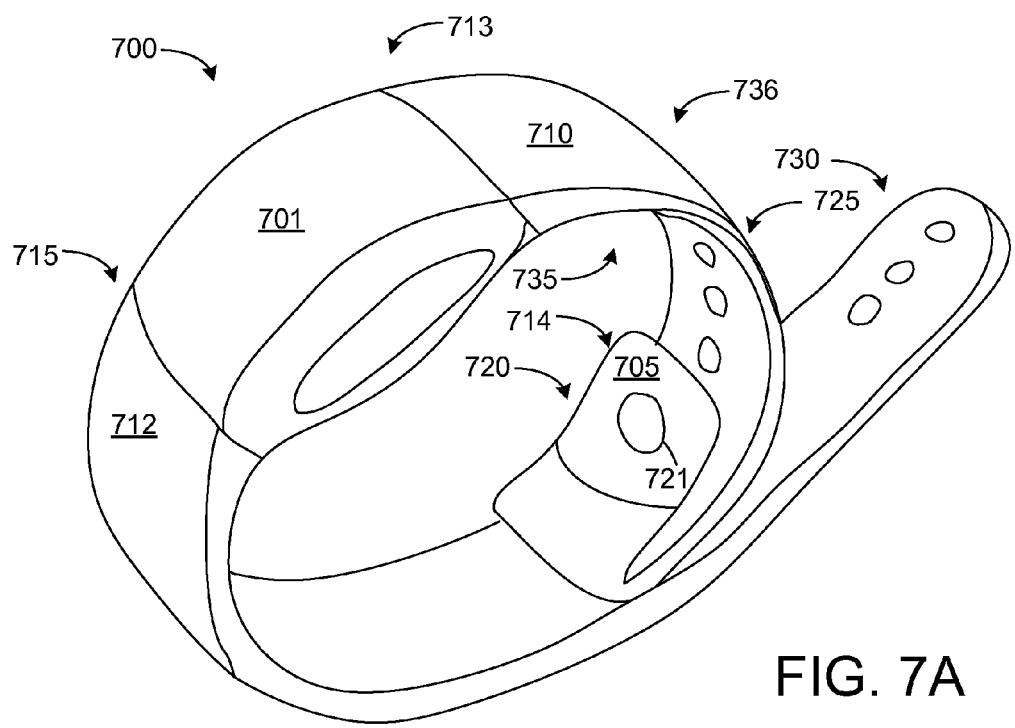
FIGS. 7A-7B show a sixth example of a manually sizable wrist-worn pressure sensing device.
Figure 7B:
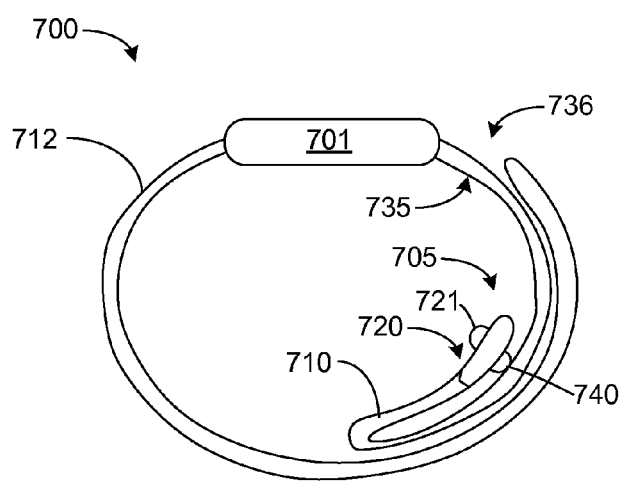

FIGS. 7A-7B show another example wearable pressure sensing device 700. Wearable pressure sensing device 700 includes primary device 701, satellite device 705, first strap 710 and second strap 712. First strap 710 is connected to primary device 701 at first end 713, and to satellite device 705 at second end 714. Second strap 712 is connected to primary device 701 at first end 715.

Satellite device 705 comprises pressure transducer assembly 720, which includes flexible cap 721 conductively coupled to a pressure transducer within pressure transducer assembly 720. Satellite device 702 is integral with first strap 710, and may thus be hard-wired to primary device 701 via wiring extending through first strap 710.

First strap 710 includes primary fastening componentry 725, while second strap 712 includes secondary fastening componentry 730 usable to adjust the circumference of wrist-worn pressure sensing device 700 without moving the fixed position of the satellite device relative to the primary device by adjustably engaging secondary fastening componentry 730 with primary fastening componentry 725. In this example, the circumference of wrist-worn pressure sensing device 700 is inversely proportionate to the amount of overlap between first strap 710 and second strap 712 when primary fastening componentry 725 is engaged with secondary fastening componentry 730.

First strap 710 comprises a first side 735 and a second side 736. The user interface (e.g., flexible cap 721) of the pressure transducer assembly may be oriented towards second side 736 when first strap 710 is in a maximally extended conformation. Second end 714 of first strap 710 may fold back towards first end 713 of first strap 710 to position satellite device 705 at a desired effective distance from primary device 701. To achieve this flexibility, first strap 710 may be made from an extremely flexible material, such as flexi-silicone. Wiring within first strap 710 may also be made from extremely flexible materials, such as ultra-flex copper wires or flex cables.

In the illustrated example, satellite device 705 is secured in place by engaging one or more notches of primary fastening componentry 725 with peg 740 extending from satellite device 705. In other implementations, a clamp, hook-and-loop fastener, or other mechanism may be used to secure the placement. In this example, primary fastening componentry 725 thus mediates both the distance between satellite device 705 and primary device 701 as well as the overall circumference of wrist-worn pressure sensing device 700. In other examples, additional fastening componentry may be included on first side 735 of first strap 710 that adjustably engages satellite device 705 to fix the position of the satellite device relative to the primary device.

Figure 8A:
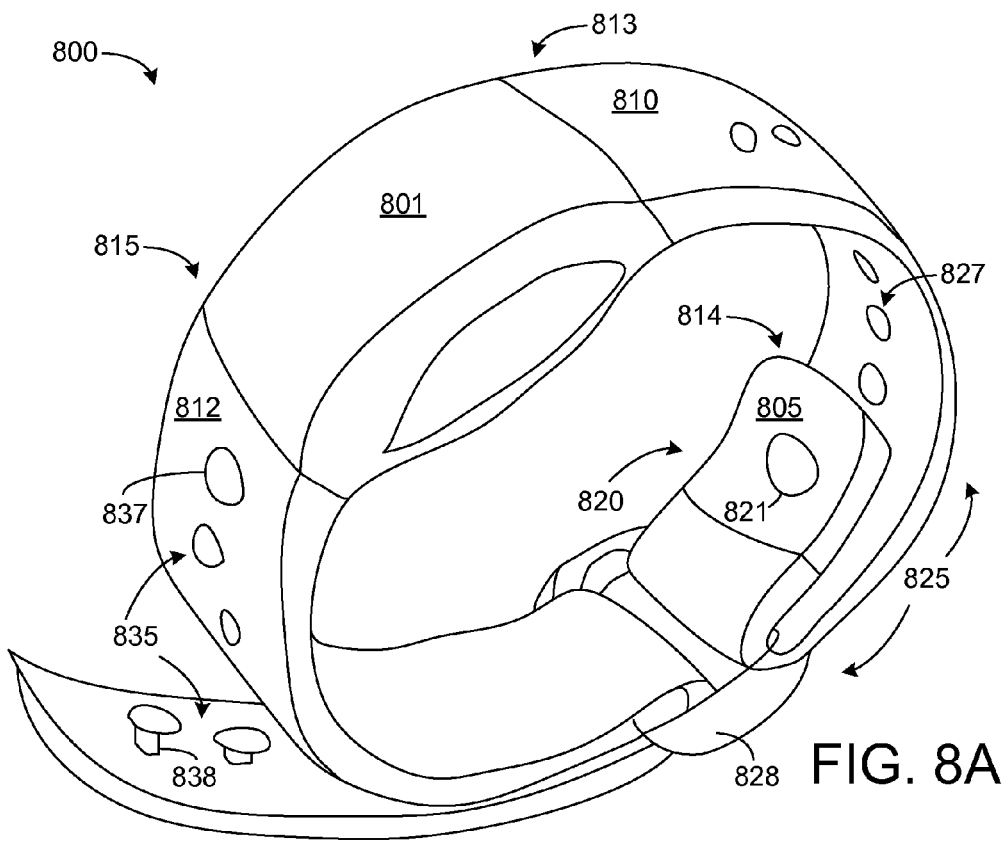
FIGS. 8A-8B show a seventh example of a manually sizable wrist-worn pressure sensing device.
Figure 8B:
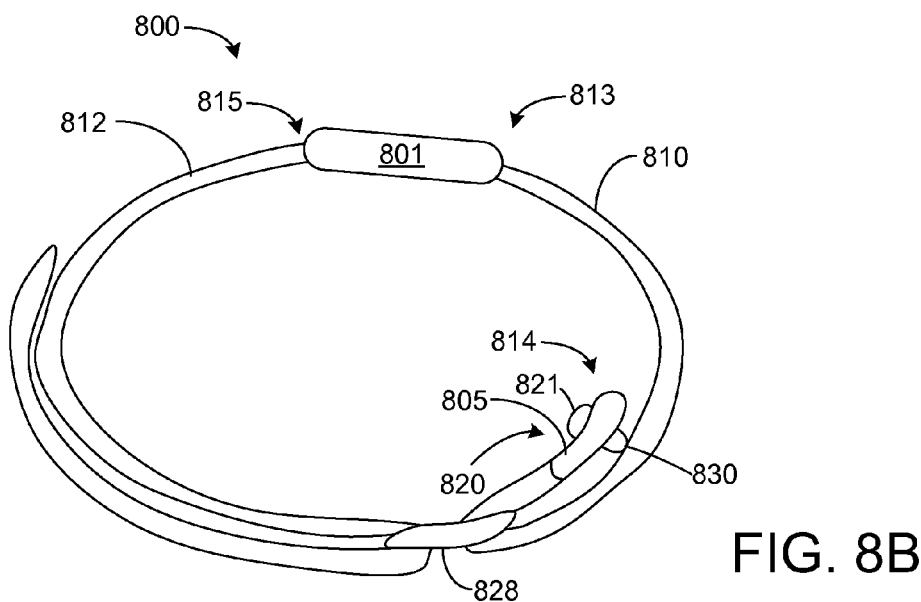

FIGS. 8A-8B show another example wearable pressure sensing device 800. Wearable pressure sensing device 800 includes primary device 801, satellite device 805, first strap 810, and second strap 812. First strap 810 is connected to primary device 801 at first end 813, and to satellite device 805 at second end 814. Second strap 812 is connected to primary device 801 at first end 815.

Satellite device 805 comprises pressure transducer assembly 820, which includes flexible cap 821 conductively coupled to a pressure transducer within pressure transducer assembly 820. Satellite device 805 is integral with first strap 810, and may thus be hard-wired to primary device 801 via wiring extending through first strap 810.

First strap 810 includes primary fastening componentry 825. In this example, primary fastening componentry 825 comprises notches 827 and buckle 828. First strap 810 may fold back on itself via buckle 828, allowing satellite device 805 to be secured in place at a sensing location at a fixed distance from primary device 801. The position of satellite device 805 may be secured in place by engaging one or more notches 827 with peg 830 extending from satellite device 805. In other implementations, a clamp, hook-and-loop fastener, or other mechanism may be used to secure the placement.

Second strap 812 includes secondary fastening componentry 835. In this example, secondary fastening componentry 835 comprises notches 837 and pegs 838. Second strap 812 may fold back on itself via buckle 828, and be secured in place by engaging one or more notches 837 with one or more pegs 838, or by other suitable fastening means. In this way, the circumference of wrist-worn pressure sensing device 800 is inversely proportionate to the amount of self-overlap along second strap 812 when primary fastening componentry 825 is engaged with secondary fastening componentry 835.

In addition to the manual sizing techniques described herein, a wrist worn pressure sensor may also comprise mechanisms for automatic/dynamic sizing. The signal quality of the pressure transducer is dependent on both positioning of the sensor relative to the radial artery, and the pressure between the sensor and the underlying tissue. Automatically resizing the band responsive to changes in signal quality and/or pressure may allow accurate pressure measurements to be maintained throughout use of the sensor.

Figure 9A:
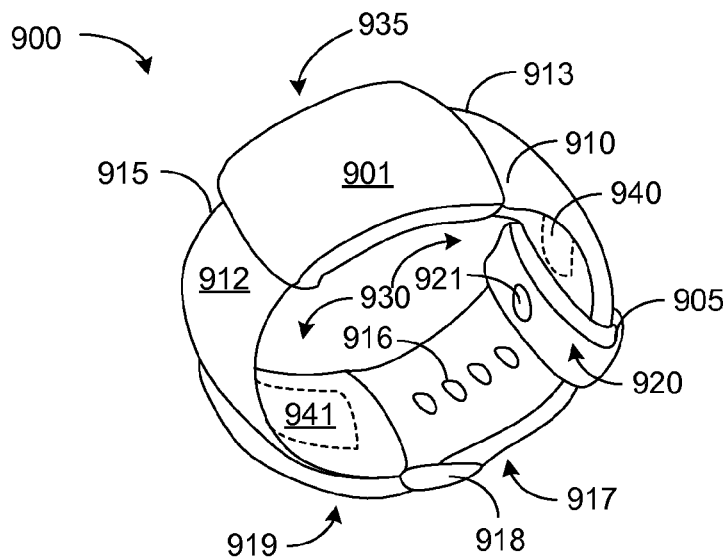
FIG. 9A shows a first example of a dynamically sizable wrist-worn pressure sensing device.

FIG. 9A illustrates a mechanism for dynamically resizing a wrist worn pressure sensing device 900. Wearable pressure sensing device 900 includes a primary device 901, a satellite device 905, first strap 910 and second strap 912. First strap 910 is connected to primary device 901 at first end 913, while second strap 912 is connected to primary device 901 at first end 915. Primary fastening componentry 916 is located at a second end 917 of first strap 910 while secondary fastening componentry 918 is located at a second end 919 of second strap 912. The straps and fastening componentry enable the wearable pressure sensing device to be closed into a loop and to be worn on a wearer's wrist. Satellite device 905 comprises pressure transducer assembly 920, which includes flexible cap 921 conductively coupled to a pressure transducer within pressure transducer assembly 920.

Wearable pressure sensing device 900 further comprises powered sizing actuators 930 configured to adjust a circumference of the wrist-worn pressure sensing device, responsive to commands received from sizing subsystem 935. In this example, the powered sizing actuators 930 include inflatable bladders 940 and 941, included in first strap 910 and second strap 912, respectively. Inflatable bladders 940 and 941 may be located within their respective straps, or may be located exterior to the straps on the user-adjacent side. Powered sizing actuators 930 may further include one or more piezo air pumps (not shown) pneumatically coupled to inflatable bladders 940 and 941. Activation of the piezo air pumps may decrease the internal diameter of wearable pressure sensing device 900 as the bladders inflate, thereby effectively increasing the thickness of straps 910 and 912.

Sizing subsystem 935 may actuate the powered sizing actuators responsive to a change in pressure between the pressure transducer assembly and the wearer's wrist. For example, sizing subsystem 935 may receive an indication of a pressure between the pressure transducer assembly and a wearer's wrist and monitor the indicated pressure for changes from a predetermined pressure range whereby signal quality from the pressure transducer assembly is acceptable (e.g., signal to noise ratio above a threshold). If the pressure between the pressure transducer assembly and the wearer's wrist decreases, sizing subsystem 935 may actuate the piezo-air pumps to inflate the inflatable bladders in order to increase the pressure between the pressure transducer assembly and the wearer's wrist. If the pressure between the pressure transducer assembly and the wearer's wrist increases, sizing subsystem 935 may release air from the inflatable bladders in order to decrease the pressure between the pressure transducer assembly and the wearer's wrist. Such sizing may be triggered by an increase or decrease above or below a threshold, for example. The inflatable bladders may be deflated via the piezo air pumps or by other suitable mechanisms, such as a pressure release valve.

Sizing subsystem 935 may also provide a wearer instruction to manually adjust a conformation of the wrist-worn pressure sensing device (e.g., by adjusting the engagement of primary fastening componentry 916 and secondary fastening componentry 918).

For most wearer s, the pressure transducers described herein are effective in similar ranges of pressure between the transducer and the underlying tissue. Thus the absolute pressure of the sensor may be used as feedback for initiating dynamic control mechanisms. Changes in ambient temperature, body temperature, elevation, etc., may cause the size of the wrist of a wearer to change slightly while wearing the pressure sensor. Changes in absolute pressure below a threshold may be mitigated by automatically adjusting a circumference of the wearable pressure sensor through activation of one or more dynamic resizing mechanisms. Changes in absolute pressure above a threshold may be countered by signaling to the wearer to adjust a position of the wearable pressure sensor. Both dynamic and manual resizing may be iterative methods. Changes in pressure transducer signal quality may also be responded to using these methods.

Although two inflatable bladders are shown, a single bladder, or more than two bladders may be included in wearable pressure sensing device 900. The placement of the bladder(s) may differ from that of inflatable bladders 940 and 941. When multiple bladders are included, sizing subsystem 935 may be configured to actuate inflation of all of the bladders simultaneously, and/or may inflate one or more of the bladders selectively. If the pressure at the pressure transducer exceeds a threshold, air may be released from one or more bladders via the piezo air pump or another mechanism.

Figure 9B:
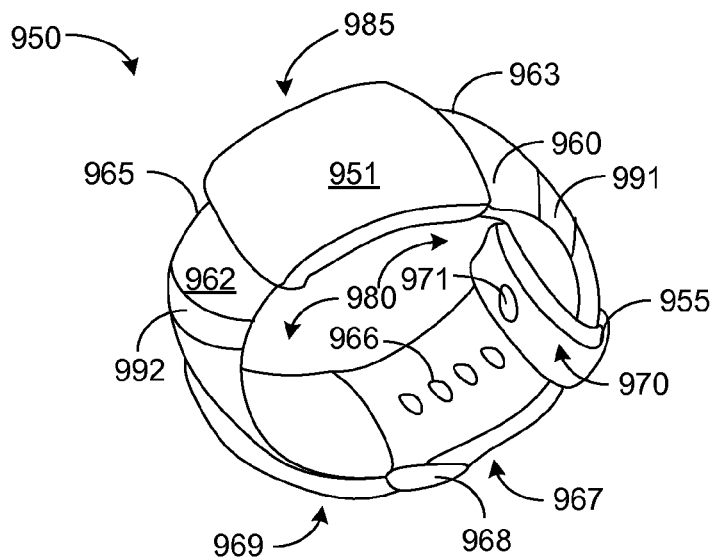
FIG. 9B shows a second example of a dynamically sizable wrist-worn pressure sensing device.

FIG. 9B illustrates an additional mechanism for dynamically resizing a wearable pressure sensing device 950. Wearable pressure sensing device 950 includes a primary device 951, a satellite device 955, first strap 960 and second strap 962. First strap 960 is connected to primary device 961 at first end 963, while second strap 962 is connected to primary device 961 at first end 965. Primary fastening componentry 966 is located at a second end 967 of first strap 960 while secondary fastening componentry 968 is located at a second end 969 of second strap 962. The straps and fastening componentry enable the wearable pressure sensing device to be closed into a loop and to be worn on a wearer's wrist. Satellite device 955 comprises pressure transducer assembly 970, which includes flexible cap 971 conductively coupled to a pressure transducer within pressure transducer assembly 970.

Wearable pressure sensing device 900 further comprises powered sizing actuators 980 configured to adjust a circumference of the wrist-worn pressure sensing device, responsive to commands received from sizing subsystem 985. In this example, the powered sizing actuators 980 include contraction regions 991 and 992, included in first strap 960 and second strap 962 respectively. Contraction regions 991 and 992 may be coupled to powered actuators, such as squiggle linear motors (not shown). Squiggle linear motors comprise a series of piezo-electric actuators attached to a stator surrounding a threaded shaft. Actuating the linear motor causes the stator to move the shaft in one of two directions. The length of the shaft-stator complex may thus expand or contract. The shafts may extend from the contraction regions into the surrounding strap. Actuation of the squiggle linear motors thereby causes the straps to change in length. This may allow the circumference of the wearable pressure sensor to be directly controlled, and the pressure between the wearable pressure sensor and the underlying tissue to be indirectly controlled.

As such, the contraction regions may contract responsive to activation of the squiggle linear motors in a first direction, and may expand responsive to activation of the one or more linear motors in a second, opposite direction. If the pressure between the pressure transducer assembly and the wearer's wrist decreases, sizing subsystem 935 may actuate the squiggle linear motors in a first direction to contract the contraction regions in order to increase the pressure between the pressure transducer assembly and the wearer's wrist. If the pressure between the pressure transducer assembly and the wearer's wrist increases, sizing subsystem 985 may actuate the squiggle linear motors in a second, opposite direction to lengthen the contraction regions, thereby decreasing the pressure between the pressure transducer assembly and the wearer's wrist.

Although two contraction regions are shown, a single contraction region, or more than two contraction regions may be included in wearable pressure sensing device 950. The placement of the contraction regions may differ from that of contraction regions 991 and 992. When multiple contraction regions are included, one or more actuators may be actuated at any one time. Further, while squiggle motors are provided as an example mechanism for dynamically changing length, any other suitable mechanism may be used.

As evident from the foregoing description, the methods and processes described herein may be tied to a sensory-and-logic system of one or more machines. Such methods and processes may be implemented as a computer-application program or service, an application-programming interface (API), a library, firmware, and/or other computer-program product. FIG. 1 shows one, non-limiting example of a sensory-and-logic system to enact the methods and processes described herein. However, these methods and process may also be enacted on sensory-and-logic systems of other configurations and form factors, as shown schematically in FIG. 10.

Figure 10:
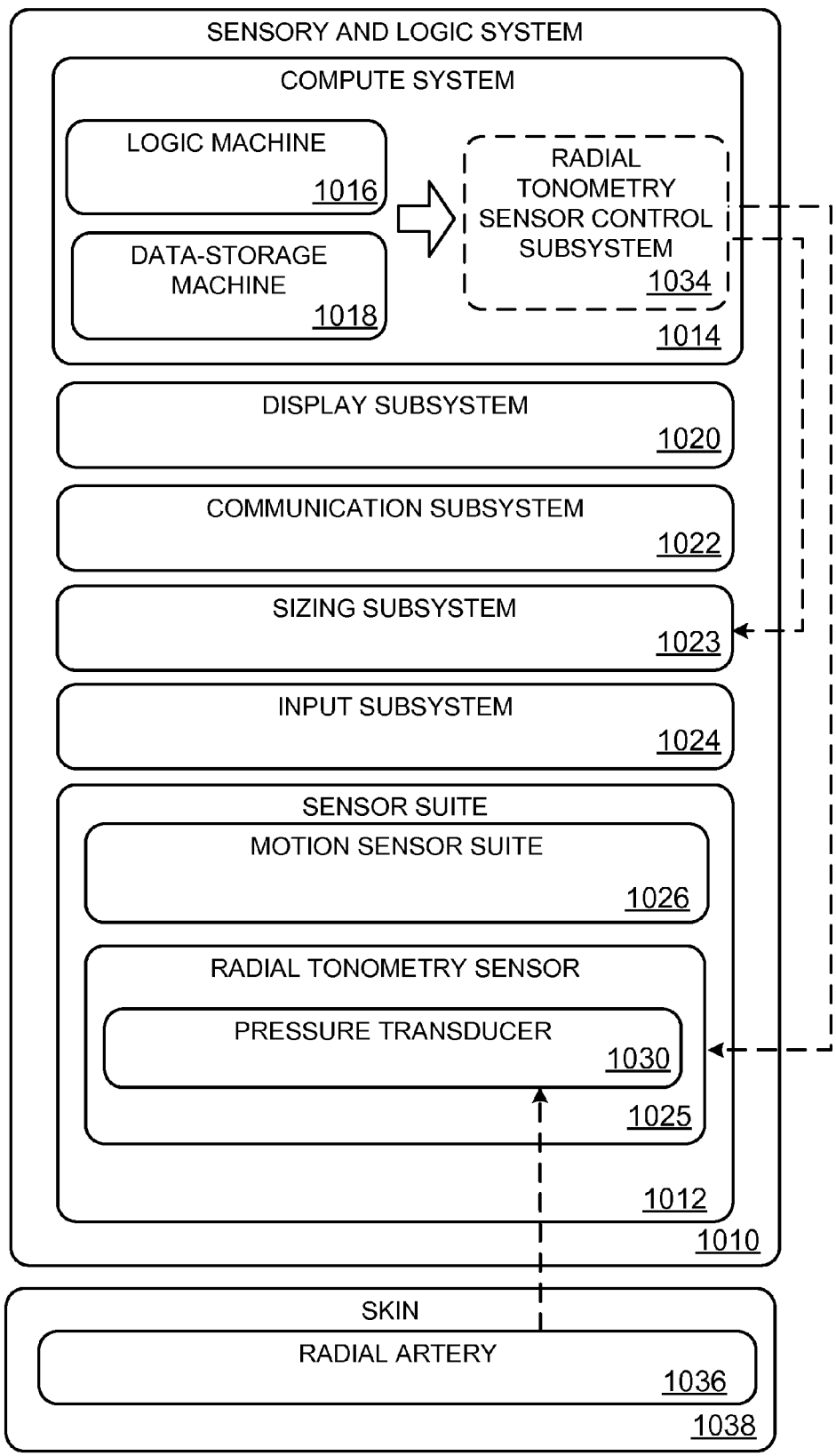
FIG. 10 schematically shows a sensory-and-logic system usable to dynamically adjust a size of a wrist-worn pressure sensing device.

FIG. 10 schematically shows a form-agnostic sensory-and-logic system 1010 that includes a sensor suite 1012 operatively coupled to a compute system 1014. The compute system includes a logic machine 1016 and a data-storage machine 1018. The compute system is operatively coupled to a display subsystem 1020, a communication subsystem 1022, a sizing subsystem 1023, an input subsystem 1024, and/or other components not shown in FIG. 10.

Logic machine 1016 includes one or more physical devices configured to execute instructions. The logic machine may be configured to execute instructions that are part of one or more applications, services, programs, routines, libraries, objects, components, data structures, or other logical constructs. Such instructions may be implemented to perform a task, implement a data type, transform the state of one or more components, achieve a technical effect, or otherwise arrive at a desired result.

Logic machine 1016 may include one or more processors configured to execute software instructions. Additionally or alternatively, the logic machine may include one or more hardware or firmware logic machines configured to execute hardware or firmware instructions. Processors of the logic machine may be single-core or multi-core, and the instructions executed thereon may be configured for sequential, parallel, and/or distributed processing. Individual components of a logic machine optionally may be distributed among two or more separate devices, which may be remotely located and/or configured for coordinated processing. Aspects of a logic machine may be virtualized and executed by remotely accessible, networked computing devices in a cloud-computing configuration.

Data-storage machine 1018 includes one or more physical devices configured to hold instructions executable by logic machine 1016 to implement the methods and processes described herein. When such methods and processes are implemented, the state of the data-storage machine may be transformed—e.g., to hold different data. The data-storage machine may include removable and/or built-in devices; it may include optical memory (e.g., CD, DVD, HD-DVD, Blu-Ray Disc, etc.), semiconductor memory (e.g., RAM, EPROM, EEPROM, etc.), and/or magnetic memory (e.g., hard-disk drive, floppy-disk drive, tape drive, MRAM, etc.), among others. The data-storage machine may include volatile, nonvolatile, dynamic, static, read/write, read-only, random-access, sequential-access, location-addressable, file-addressable, and/or content-addressable devices.

Data-storage machine 1018 includes one or more physical devices. However, aspects of the instructions described herein alternatively may be propagated by a communication medium (e.g., an electromagnetic signal, an optical signal, etc.) that is not held by a physical device for a finite duration.

Aspects of logic machine 1016 and data-storage machine 1018 may be integrated together into one or more hardware-logic components. Such hardware-logic components may include field-programmable gate arrays (FPGAs), program- and application-specific integrated circuits (PASIC/ASICs), program- and application-specific standard products (PSSP/ASSPs), system-on-a-chip (SOC), and complex programmable logic devices (CPLDs), for example.

Display subsystem 1020 may be used to present a visual representation of data held by data-storage machine 1018. This visual representation may take the form of a graphical user interface (GUI). As the herein described methods and processes change the data held by the storage machine, and thus transform the state of the storage machine, the state of display subsystem 1020 may likewise be transformed to visually represent changes in the underlying data. Display subsystem 1020 may include one or more display subsystem devices utilizing virtually any type of technology. Such display subsystem devices may be combined with logic machine 1016 and/or data-storage machine 1018 in a shared enclosure, or such display subsystem devices may be peripheral display subsystem devices. Display 34 of FIG. 1 is an example of display subsystem 1020.

Communication subsystem 1022 may be configured to communicatively couple compute system 1014 to one or more other computing devices. The communication subsystem may include wired and/or wireless communication devices compatible with one or more different communication protocols. As non-limiting examples, the communication subsystem may be configured for communication via a wireless telephone network, a local- or wide-area network, and/or the Internet. Communication suite 36 of FIG. 1 is an example of communication subsystem 1022.

Input subsystem 1024 may comprise or interface with one or more user-input devices such as a keyboard, touch screen, button, dial, joystick, or switch. In some embodiments, the input subsystem may comprise or interface with selected natural user input (NUI) componentry. Such componentry may be integrated or peripheral, and the transduction and/or processing of input actions may be handled on- or off-board. Example NUI componentry may include a microphone for speech and/or voice recognition; an infrared, color, stereoscopic, and/or depth camera for machine vision and/or gesture recognition; a head tracker, eye tracker, accelerometer, and/or gyroscope for motion detection and/or intent recognition. Push button 48 of FIG. 1 is an example of input subsystem 1024.

Sensor suite 1012 may include one or more different sensors—e.g., radial tonometry sensor 1025, a touch-screen sensor, pushbutton sensor, microphone, visible-light sensor, ultraviolet sensor, ambient-temperature sensor, contact sensors, and/or GPS receiver—as described above with reference to FIG. 1. Sensor suite 1012 may include motion sensor suite 1026. Motion sensor suite 1026 may include one or more of an accelerometer, gyroscope, magnetometer, or other suitable motion detectors.

As described herein, radial tonometry sensor 1025 may include pressure transducer 1030. Compute system 1014 may include radial tonometry control subsystem 1034, which may be communicatively coupled to logic machine

1016 and data-storage machine 1018. Pressure transducer 1030 may comprise one or more piezo-resistive sensors configured to provide absolute pressure signals to compute system 1014 via an analog-to-digital converter. Pressure transducer 1030 may be configured to transduce pressure waves from the radial artery 1036 through the skin 1038 of the wearer.

Radial tonometry control subsystem 1034 may further process the raw signals to determine heart rate, blood pressure, caloric expenditures, etc. Processed signals may be stored and output via compute system 1014. Control signals sent to radial tonometry sensor 1025 may be based on signals received from pressure transducer 1030, signals derived from sensor suite 1012, information stored in data-storage machine 1018, input received from communication subsystem 1022, input received from input subsystem 1024, etc.

Sizing subsystem 1023 includes one or actuators for dynamically adjusting the size of components configured to affix sensory- and -logic system 1010 to a wrist of a wearer. Inflatable bladders 940 and 941, and contraction regions 991 and 992 are examples of such actuators. Sizing subsystem 1023 may activate one or more actuators responsive to signals from radial tonometry sensor control subsystem 1034. In some examples, sizing subsystem 1023 may receive signals directly from radial tonometry sensor 1025 and/or pressure transducer 1030.

In an example, a wrist-worn pressure sensing device comprises: a primary device; a pressure sensor; a first strap adjustable to fix a position of the pressure sensor relative to the primary device, the first strap comprising: a first end connected to the primary device; a second end connected to the pressure sensor; and primary fastening componentry; and a second strap comprising: a first end connected to the primary device; and secondary fastening componentry usable to adjust a circumference of the wrist-worn pressure sensing device without moving the fixed position of the pressure sensor relative to the primary device by adjustably engaging the secondary fastening componentry with the primary fastening componentry. In this example or any other example, the pressure sensor is communicatively coupled to a compute machine located within the primary device via the first strap. In this example or any other example, the second end of the first strap folds back towards the first end of the first strap to position the pressure sensor at a desired effective distance from the primary device. In this example or any other example, the circumference of the wrist-worn pressure sensing device is inversely proportionate to an amount of overlap between the first strap and the second strap when the primary fastening componentry is engaged with secondary fastening componentry. In this example or any other example, the circumference of the wrist-worn pressure sensing device is inversely proportionate to an amount of self-overlap along the second strap when the primary fastening componentry is engaged with secondary fastening componentry. In this example or any other example, the position of the pressure sensor relative to the primary device is adjustable by physically altering a length of the first strap, while maintaining connective componentry of the first strap that mediates connecting the first end of the first strap to the primary device and the second end of the first strap to the pressure sensor.

In an example, a wrist-worn pressure sensing device comprises: a primary device; a first strap comprising: a first end connected to the primary device; primary fastening componentry; and a plurality of possible sensing locations, each possible sensing location having a different effective distance from the primary device along the first strap; a pressure sensor adjustably connected to the first strap at a selected sensing location of the plurality of possible sensing locations, the pressure sensor having a fixed position relative to the primary device when connected to the first strap; and a second strap comprising: a first end connected to the primary device; and secondary fastening componentry usable to adjust a circumference of the wrist-worn pressure sensing device without moving the pressure sensor from the selected sensing location by adjustably engaging the secondary fastening componentry with the primary fastening componentry. In this example or any other example, the device further comprises: a satellite device configured to attach the pressure sensor to the first strap, and further configured to mediate communication between the pressure sensor and a compute device situated within the primary device. In this example or any other example, the first strap further comprises one or more conducting wires extending from the primary device through the plurality of possible sensing locations, and wherein the satellite device includes one or more conductive contacts that interface with the one or more conducting wires when the satellite device is attached to the first strap at the selected sensing location of the plurality of possible sensing locations. In this example or any other example, each of the one or more conductive wires are located within a slit of the first strap. In this example or any other example, the one or more conductive wires are located on an interior of the first strap, and wherein the satellite device includes one or more piercing conductive contacts configured to penetrate the first strap when the satellite device is attached to the first strap. In this example or any other example, the plurality of possible sensing locations are located within a groove of the first strap. In this example or any other example, the device further comprises an energy-storage device coupled within the primary device, and wherein the satellite device is further configured to transfer power from the energy-storage device to the pressure sensor via the first strap. In this example or any other example, the primary device further comprises one or more inductive coils, and wherein the satellite device includes one or more inductive coils enabling one or more of wireless power transfer and wireless communication.

In an example, a wrist-worn pressure sensing device comprises: a primary device; a first strap connected to the primary device; a pressure sensor coupled to the first strap at a fixed position relative to the primary device; a second strap connected to the primary device, the second strap comprising fastening componentry usable to adjust a circumference of the wrist-worn pressure sensing device without moving the fixed position of the pressure sensor relative to the primary device; powered sizing actuators configured to adjust a circumference of the wrist-worn pressure sensing device; and a sizing subsystem to actuate the powered sizing actuators responsive to a change in pressure between the pressure sensor and a wearer's wrist. In this example or any other example, the sizing subsystem is further configured to: receive from the pressure sensor an indication of a pressure between the pressure sensor and the wearer's wrist; and provide a user instruction to manually adjust a conformation of the wrist-worn pressure sensing device relative to the wearer's wrist. In this example or any other example, the powered sizing actuators comprise: one or more inflatable bladders pneumatically connected to a piezo air pump. In this example or any other example, the sizing subsystem is further configured to: actuate the piezo air pump responsive to a decrease in pressure between the pressure sensor and the wearer's wrist; and release air from the one or more inflatable bladders responsive to an increase in pressure between the pressure sensor and the wearer's wrist. In this example or any other example, the powered sizing actuators comprise: one or more linear motors coupled to one or more of the first strap and second strap within one or more contraction regions, the contraction regions configured to contract responsive to activation of the one or more linear motors in a first direction, and further configured to expand responsive to activation of the one or more linear motors in a second, opposite direction. In this example or any other example, the sizing subsystem is further configured to: actuate the one or more linear motors in the first direction responsive to a decrease in pressure between the pressure sensor and the wearer's wrist; and actuate the linear motors in the second direction responsive to an increase in pressure between the pressure sensor and the wearer's wrist.

The configurations and approaches described herein are exemplary in nature, and that these specific implementations or examples are not to be taken in a limiting sense, because numerous variations are feasible. The specific routines or methods described herein may represent one or more processing strategies. As such, various acts shown or described may be performed in the sequence shown or described, in other sequences, in parallel, or omitted.

The subject matter of this disclosure includes all novel and non-obvious combinations and sub-combinations of the various processes, systems and configurations, and other features, functions, acts, and/or properties disclosed herein, as well as any and all equivalents thereof.

The invention claimed is:

1. A wrist-worn pressure sensing device, comprising:
a primary device;
a pressure sensor;
a first strap foldable to fix a position of the pressure sensor along the length of the first strap relative to the primary device, the first strap comprising:
   a first end connected to the primary device;
   a second end connected to the pressure sensor and configured to fold back towards the first end, wherein a relative position of a fold along the length of the first strap dictates the position of the pressure sensor along the length of the first strap relative to the primary device; and
   primary fastening componentry; and
a second strap comprising:
   a first end connected to the primary device; and
   secondary fastening componentry usable to adjust a circumference of the wrist-worn pressure sensing device without moving the fixed position of the pressure sensor along the length of the first strap relative to the primary device by adjustably engaging the secondary fastening componentry with the primary fastening componentry.

2. The wrist-worn pressure sensing device of claim 1, wherein the pressure sensor is communicatively coupled to a compute machine located within the primary device via the first strap.

3. The wrist-worn pressure sensing device of claim 1, wherein the second end of the first strap folds back towards the first end of the first strap to position the pressure sensor at a fixed distance along the length of the first strap from the primary device.

4. The wrist-worn pressure sensing device of claim 1, wherein the circumference of the wrist-worn pressure sensing device is inversely proportionate to an amount of overlap between the first strap and the second strap when the primary fastening componentry is engaged with the secondary fastening componentry.

5. The wrist-worn pressure sensing device of claim 1, wherein the circumference of the wrist-worn pressure sensing device is inversely proportionate to an amount of self-overlap along the second strap when the primary fastening componentry is engaged with the secondary fastening componentry.

* * * * *